United States Patent [19]

Levesque et al.

[11] Patent Number: 5,114,647
[45] Date of Patent: May 19, 1992

[54] EFFERVESCENT TABLETS HAVING INCREASED DISINTEGRATION RATES

[75] Inventors: Kenneth J. Levesque, Bristol; Roy P. Alexander, Killingworth, both of Conn.

[73] Assignee: Olin Corporation, Cheshire, Conn.

[21] Appl. No.: 648,948

[22] Filed: Feb. 1, 1991

[51] Int. Cl.⁵ ............................................. B29C 43/02
[52] U.S. Cl. .............................. 264/115; 252/186.35; 252/187.34; 264/118; 264/120; 264/122
[58] Field of Search ............... 264/115, 118, 120, 122; 252/186.2, 186.35, 187.33, 187.34

[56] References Cited

U.S. PATENT DOCUMENTS

| | | | |
|---|---|---|---|
| 3,336,228 | 8/1967 | Fuchs et al. | 252/187.34 |
| 3,769,224 | 10/1973 | Inamorato | 252/187.34 |
| 3,886,249 | 5/1975 | Manganaro | 264/118 |
| 4,261,942 | 4/1981 | Shimamura et al. | 264/118 |
| 4,265,847 | 5/1981 | Hunt et al. | 264/122 |
| 4,389,318 | 6/1983 | Wojtowicz | 210/755 |
| 4,557,926 | 12/1985 | Nelson et al. | 424/409 |
| 4,654,341 | 3/1987 | Nelson et al. | 514/241 |
| 4,762,637 | 8/1988 | Aronson et al. | 252/99 |
| 4,897,257 | 1/1990 | Nishikawa et al. | 424/44 |
| 4,909,956 | 3/1990 | Webber | 252/187.34 |

FOREIGN PATENT DOCUMENTS 739740 of 1973 South Africa.

OTHER PUBLICATIONS

Olin Surfactants Product Data Bulletin, 1990 Olin Corporation Poly-Tergent® 3B2 Acid and 3B2 Anionic Surfactant.

*Primary Examiner*—Mary Lynn Theisen
*Attorney, Agent, or Firm*—James B. Haglind; Paul Weinstein

[57] ABSTRACT

A method for producing sanitizing compositions in compressed form which includes:

a) admixing an alkali metal carbonate with a solid water soluble aliphatic carboxylic acid to form an acidic mixture.

b) compressing the acidic mixture to produce a compressed form of the acidic mixture, c) crushing the compressed form to produce granules of the acidic mixture, and.

d) admixing granules of the acidic mixture with an alkali metal chloroisocyanurate, and an alkali metal bicarbonate to produce a sanitizing composition.

19 Claims, 2 Drawing Sheets

EFFERVESCENT TABLETS HAVING INCREASED DISINTEGRATION RATES

FIELD OF THE INVENTION

This invention is related to compositions for sanitizing water bodies. More particularly, this invention is related to compositions having increased rates of disintegration for sanitizing water bodies.

BACKGROUND OF THE INVENTION

A number of different compositions and methods have been proposed for preparing bleaching, cleaning, disinfecting and sanitizing solutions. These include compositions containing available chlorine such as various solid hypochlorite and chloramine compositions which can be employed as granules, but are more commonly employed as tablets.

In order to act effectively as a sanitizing agent, it is desired that the composition disintegrate quickly to form hypochlorous acid or hypochlorite ions. Solid hypochlorite compositions include alkali metal hypochlorites such as lithium hypochlorite as well as alkaline earth hypochlorites, for example, calcium hypochlorite and dibasic magnesium hypochlorite.

Chloramine compositions which are suitable include solid chloroisocyanurate compositions, i.e., those containing trichloroisocyanuric acid, dichloroisocyanuric acid, salts of dichloroisocyanuric acid such as alkali metal dichloroisocyanurates and alkaline earth metal dichloroisocyanurates as well as complexes and mixtures thereof.

Tablets having a high proportion of a chloramine composition such as trichloroisocyanuric acid or dichloroisocyanuric acid or its alkali salts have the disadvantage that they dissolve relatively slowly in cold water. It is known to include in these chloramine tablets additives such alkali metal carbonates or bicarbonates and solid organic acids as disintegration agents. When water is added, carbon dioxide is freed which encourages the disintegration and dissolution of the tablets. While tablets including these additives dissolve rapidly in warm water, their rate of dissolution in cold water is not substantially greater than that of dichloroisocyanuric acid or its alkali metal salts.

South African patent No. 73-9740, issued to Henkel & Cie teaches making readily soluble tablets by mixing dichloroisocyanuric acid or its alkali metal salts with starches such as potato, maize, wheat or rice starch, or starches which have been chemically partially reduced, peptized, or carboxymethylated. These tablets are used for the production of bleaching and disinfecting solutions, for example, for textiles, cleansing and rinsing preparations, alkaline bottle cleaners and mechanical dish washer preparations. The tablets can contain from 2.5 to 18 percent by weight of the starch and 80-97 percent by weight of sodium or potassium dichloroisocyanurate. While the addition of a starch does increase the rate of solubility of the tablets, the resulting solutions are not clear.

BRIEF SUMMARY OF THE INVENTION

Figure 1:
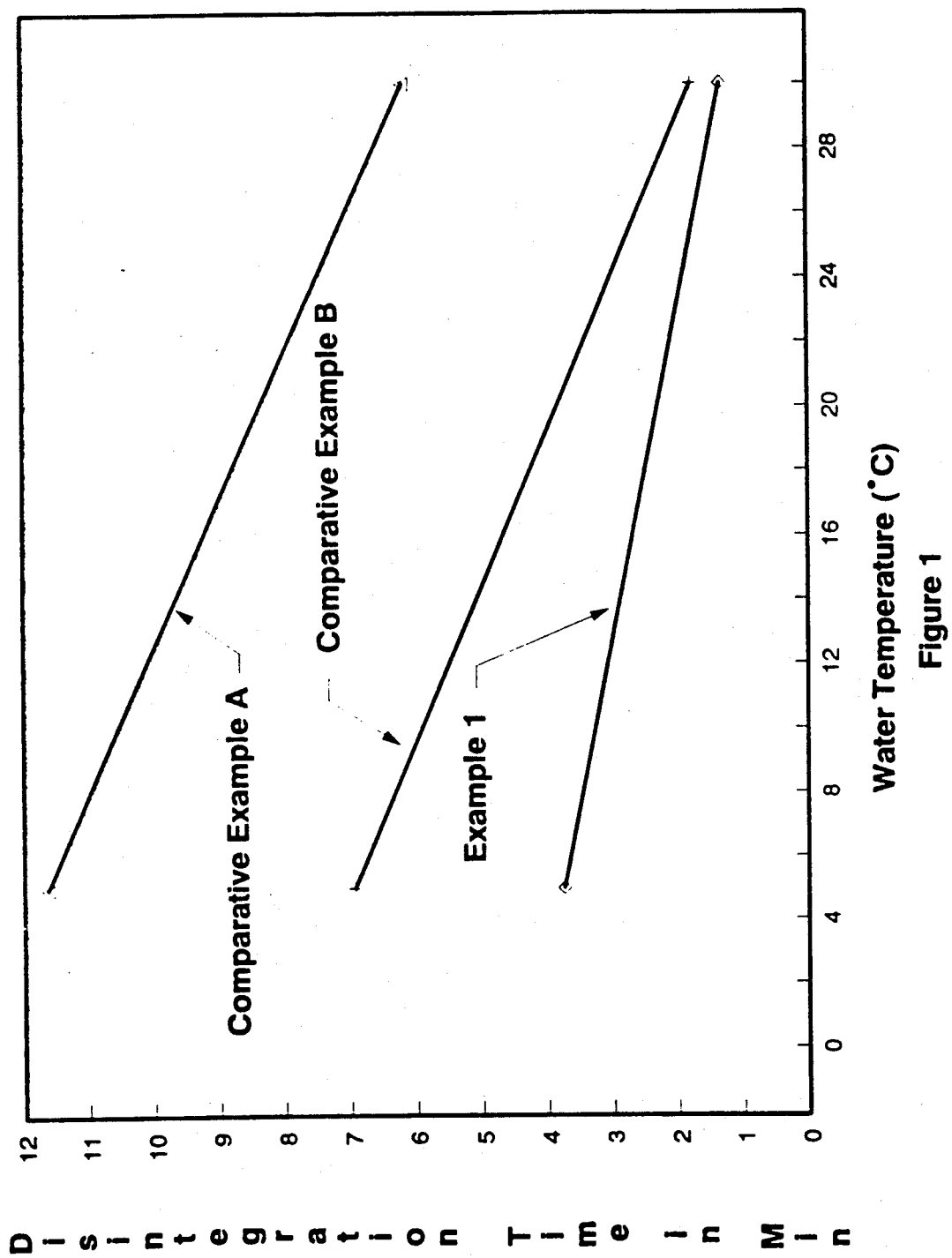
FIG. 1 is a graph depicting the disintegration times of the embodiment of Example 1, made by the method of the invention, and those of Comparative Examples A and B.

It is therefore an object of the invention to develop a tablet which contains active chlorine compounds, is simple to produce, dissolves or disintegrates within a short time, even in cold water, and has minimal losses of active chlorine or increases in dissolving or disintegration time after prolonged periods of storage.

A further object of the present invention is to provide a tablet for preparing sanitizing, cleaning or bleaching solutions which dissolves or disintegrates rapidly to give a clear solution.

These and other objects of the invention are accomplished in a method for producing sanitizing compositions in compressed form which comprises:
a) admixing an alkali metal carbonate with a solid water soluble aliphatic carboxylic acid to form an acidic mixture,
b) compressing the acidic mixture to produce a compressed form of the acidic mixture,
c) crushing the compressed form to produce granules of the acidic mixture, and,
d) admixing granules of the acidic mixture with an alkali metal chloroisocyanurate, and an alkali metal bicarbonate to produce a sanitizing composition.

DETAILED DESCRIPTION OF THE INVENTION

The novel method of the present invention employs as one component of the rapidly dissolving sanitizing composition, a mixture of an alkali metal carbonate with a solid water-soluble aliphatic carboxylic acid. The alkali metal carbonate is, for example, sodium carbonate or potassium carbonate and the granular forms of these compounds which are available commercially are quite satisfactory.

Any solid aliphatic carboxylic acid can be employed which is soluble in water, and particularly cold water. Preferred as the solid water-soluble aliphatic carboxylic acid are polycarboxylic acids, including, for example, citric acid, adipic acid, tartaric acid, oxalic acid, and mixtures thereof. Commercial solid aliphatic carboxylic acids in granular or powder form are quite suitable for use. The alkali metal carbonate and the solid water-soluble aliphatic carboxylic acid are admixed and compacted by known compression methods to produce tablets, briquettes, disks, and the like, of the acidic mixture.

The acidic mixture contains, for example, weight ratios of an alkali metal carbonate such as sodium or potassium carbonate to the solid water-soluble aliphatic dicarboxylic acid of from about 0.05:1 to about 0.9:1, and preferably from about 0.1:1 to about 0.4:1.

To provide granules of the acidic mixture, the compressed forms are crushed by any suitable method which minimizes the amount of fines or powder produced. Granules of the acid mixture are, for example, screened to a particle size in the range of from about −10 to about +100 mesh (2,000 to about 150 microns) and, preferably, from about −16 to about +60 mesh (1,000 to about 250 microns). The granules of the acidic mixture are then admixed with the other components; that is, the alkali metal dichloroisocyanurate and the alkali metal bicarbonate. The order of addition of these components is not critical and any suitable order may be employed.

As alkali metal dichloroisocyanurates, sodium dichloroisocyanurate and potassium dichloroisocyanurate and hydrates thereof may be used, with sodium dichloroisocyanurate and being preferred. Similarly, the alkali metal bicarbonates may be sodium or potassium bicarbonate with sodium bicarbonate being preferred.

The compositions may have any suitable available chlorine concentration. For example, compositions having available chlorine concentrations of from about 10 to about 60 percent are readily prepared by the novel method of the invention.

The sanitizing mixture produced is then compressed by any suitable commercial method to produce, for example, tablets, rings, disks, sticks, briquets, etc. Preferred embodiments of the compressed forms are tablets, disks and briquets, with tablets being particularly preferred. The sanitizing compositions produced by the novel process of the present invention rapidly disintegrate when placed in water to sanitize the water without imparting cloudiness or opaqueness to the sanitized water. Surprisingly, the compressed forms of the sanitizing compositions rapidly disintegrate in cold water which is present, for example, in toilet bowls to produce clear solutions.

To provide the compositions with increased cleaning action, it may be desirable to incorporate in the composition, a surfactant. Any surfactant may be used which is compatible with available chlorine-containing sanitizing agents. Suitable surfactants include anionic surfactants such as sodium lauryl sulfate and alkyl diphenylether disulfonic acid and its salts, as well as nonionic surfactants such as benzyl ethers of alkylphenol alkoxylates, among others. The amount of surfactant used is not critical and the amount employed may vary depending on the specific application. Typical amounts include those in the range of from about 0.1 to about 20%, and preferably from about 1 to about 10% by weight.

However, the addition of the surfactant to the sanitizing composition significantly increases the dissolving or disintegration time of the compressed form. To incorporate the surfactant into the tablet while minimizing the increase and in dissolving or disintegration time, it has been found that employing the novel method of the present invention, the surfactant can be compacted or admixed with the aliphaticcarboxylic acid component or the alkali metal carbonate component. Compressed forms of the surfactant-containing composition disintegrate and dissolve to form a clear sanitizing solution.

Where the surfactant-containing composition is to be used in cold water, it may be desirable to incorporate a starch composition. The starch is added directly and is not pre-mixed with any of the other components of the surfactant-containing composition. Suitable starches which may be employed include amylose and amylopectin containing starches such as corn, maize, tapioca, potato or rice starch, as well as starches which have been chemically modified including oxidized starches, acid-modified starches, soluble starches, starch ethers, and the like. When the starch is employed in the surfactant-containing composition, it is used in small amounts, for example, from about 0.1 to about 5 percent by weight.

The novel method of the present invention produces sanitizing compositions which rapidly disintegrate and dissolve, even in cold water, to provide bleaching, cleaning, and sanitizing solutions.

The method of the present invention is illustrated by the following Examples with no intention of being limited thereby. Unless otherwise indicated, all parts and percentages are by weight.

EXAMPLE 1

Adipic acid (Food processing quality, E. I. DuPont de Nemours, Wilmington, Del.)(2.8636 g) and 0.6364 g of sodium carbonate (Anhydrous granular, J. T. Baker, Inc., Phillipsburg, N.J.) were added to a container and mixed by agitating the container. The mixture was then compressed into tablets on a Carver press (Laboratory press, model C, Sterling, Inc., Menomonee, Wis.). The press had a 0.75 inch stainless steel tabletting die which was lubricated with sodium stearate (OP-100, RTD Chemicals, Hackettstown, N.J.). The tablets were produced at a force of 10,000 pounds for a period of 20 seconds. The tablets, containing approximately 3.5 g of acid mixture, were then ground in a mortar and pestle to granules and the granules screened to select those having a size in the range of $-16$ to $+60$ mesh. Granules (0.9625 g) containing the mixture of sodium carbonate and adipic acid were then admixed with 1.7500 g of sodium dichloroisocyanurate (CDB-63 ® Olin Corporation, Stamford, Conn.) and 0.7875 g of sodium bicarbonate (Fisher Scientific, Pittsburgh, Pa.). Following mixing, tablets of the mixture were produced on the Carver press at a compression of 3500 pounds force for 5 seconds. The tablets contained approximately 3.5 g of the mixture.

To determine the disintegration time, a tablet of the mixture was placed in a container filled with tap water at 5° C. and the time measured for the tablet to completely disintegrate. During the disintegration period considerable effervescence occurred. After 3 minutes, effervescence ceased and the tablet had totally disintegrated to provide a clear sanitizing solution.

A second tablet was placed in a container of tap water at a temperature of 30° C. After 1.33 minutes, effervescence ceased and the tablet has totally disintegrated to form a clear solution. The results are depicted on FIG. 1.

COMPARATIVE EXAMPLE A

Adipic acid (1.7500 g) and 1.7500 g of sodium bicarbonate were mixed and the mixture was then compressed into tablets on the Carver press using a 0.75 inch stainless steel tabletting die. The die was lubricated periodically with sodium stearate. The tablets were produced at a force of 10,000 pounds for a period of 20 seconds. The tablets, containing approximately 3.5 g of acid mixture, were then ground in a mortar and pestle to granules and the granules screened to select those having a size in the range of $-16$ to $+60$ mesh. Granules containing the mixture of sodium bicarbonate and adipic acid (1.5750 g) were then mixed with 1.7500 g of sodium dichloroisocyanurate and 0.1750 g of sodium carbonate. Following mixing, tablets of the mixture were produced on the Carver press at a compression of 3500 pounds force for 5 seconds. The tablets contained approximately 3.5 g of the mixture.

To determine the disintegration time, a tablet of the mixture was placed in a container filled with tap water at 5° C. and the time measured for the tablet to completely disintegrate. During the disintegration period considerable effervescence occurred. After 11.63 minutes, effervescence ceased, the tablet had totally disintegrated, and the resulting solution was clear.

A second tablet was placed in a container of tap water at a temperature of 30° C. After 6.17 minutes, effervescence ceased and the tablet had totally disintegrated to form a clear solution. The results are depicted on FIG. 1.

COMPARATIVE EXAMPLE B

Adipic acid (0.7875 g) 0.7875 g of sodium bicarbonate, 1.7500 g of sodium dichloroisocyanurate and 0.1750 g of sodium carbonate were mixed and the mixture was then compressed into tablets on the Carver press using a 0.75 inch stainless steel tabletting die. The die was lubricated periodically with sodium stearate. The tablets were produced at a compression of 3500 pounds force for 5 seconds. The tablets contained approximately 3.5 g of the mixture.

To determine the disintegration time, a tablet of the mixture was placed in a container filler with tap water at 5° C. and the time measured for the tablet to completely disintegrate. During the disintegration period considerable effervescence occurred. After 6.93 minutes, effervescence ceased, the tablet had totally disintegrated, and the resulting solution was clear.

A second tablet was placed in a container of tap water at a temperature of 30° C. After 1.77 minutes, effervescence ceased and the tablet had totally disintegrated to form a clear solution. The results are depicted on FIG. 1.

As shown in FIG. 1, the method of the invention produced tablets having significantly decreased disintegration times in cold water (at least 50%) over tablets produced by the methods of Comparative Examples A and B.

EXAMPLE 2

Adipic acid (3.0882 g) and 0.4118 g of decyl diphenyl ether disulfonic acid, sodium salt (Poly-Tergent ® 3B2, Olin Corporation, Stamford, Conn.) were mixed and the mixture was then compressed into tablets on the Carver press. The press had a 0.75 inch stainless steel tabletting die which was lubricated with sodium stearate. The tablets were produced at a force of 10,000 pounds for a period of 20 seconds. The tablets containing approximately 3.5 g of surfactant acid mixture were then ground in a mortar and pestle to granules and the granules screened to select those having a size in the range of −16 to +60 mesh. Granules (0.8925 g) containing the mixture of Poly-Tergent ® 3B2 and adipic acid were then mixed with 1.5925 g of sodium dichloroisocyanurate, 0.7875 g of sodium bicarbonate, 0.1750 g sodium carbonate, and 0.0525 g soluble starch (Analytical reagent, Mallinckrodt, Inc., St. Louis, Mo.). Following mixing, tablets of the mixture were produced on the Carver press at a compression of 3500 pounds force for 5 seconds. The tablets contained approximately 3.5 g of the mixture.

Figure 2:
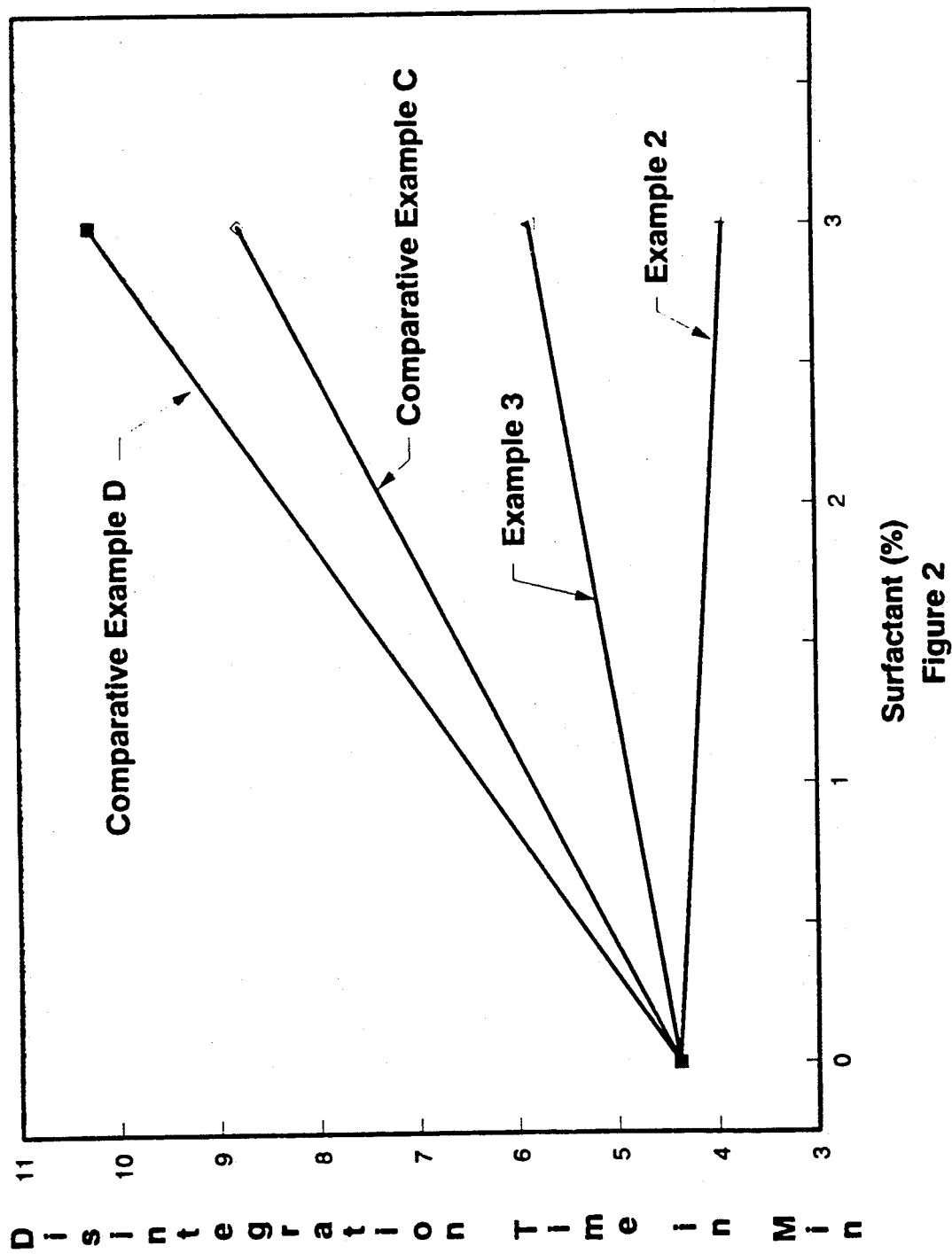
FIG. 2 is a graph showing the disintegration times of the embodiments of Examples 2 and 3 prepared by the method of the invention, and those of Comparative Examples C and D.

To determine the disintegration time, a tablet of the mixture was placed in a container filled with tap water at 5° C. and the time measured for the tablet to completely disintegrate. During the disintegration period considerable effervescence occurred. After 3.90 minutes, effervescence ceased and the tablet had totally dissolved to provide a clear sanitizing solution. The results are illustrated on FIG. 2.

COMPARATIVE EXAMPLE C

Sodium bicarbonate (3.0882 g) and 0.4118 g of Poly-Tergent ® 3B2 were mixed and the mixture was then compressed into tablets on the Carver press using a 0.75 inch stainless steel tabletting die. The die was lubricated periodically with sodium stearate. The tablets were produced at a force of 10,000 pounds for a period of 20 seconds. The tablets, containing approximately 3.5 g of the surfactant bicarbonate mixture, were then ground in a mortar and pestle to granules and the granules screened to select those having a size in the range of −16 to +60 mesh. Granules containing the mixture of sodium bicarbonate and Poly-Tergent ® 3B2 (0.8925 g) were then mixed with 1.5925 g of sodium dichloroisocyanurate, 0.1750 g of $Na_2CO_3$, 0.7875 g of adipic acid, and 0.0525 g soluble starch. Following mixing, tablets of the mixture were produced on the Carver press at a compression of 3500 pounds force for 5 seconds. The tablets contained approximately 3.5 g of the mixture.

To determine the disintegration time, a tablet of the mixture was placed in a container filled with tap water at 5° C. and the time measured for the tablet to completely disintegrate. During the disintegration period considerable effervescence occurred. After 8.76 minutes, effervescence ceased, the tablet had totally disintegrated and the resulting solution was clear. The results are illustrated on FIG. 2.

COMPARATIVE EXAMPLE D

Adipic acid (0.7875 g), 0.7875 g of sodium bicarbonate, 1.5925 g of sodium dichloroisocyanurate, 0.1750 g of sodium carbonate, 0.0525 g soluble starch, and 0.1050 g of Poly-Tergent ® 3B2 were mixed and the mixture was then compressed into tablets on the Carver press using a 0.75 inch stainless steel tabletting die. The die was lubricated periodically with sodium stearate. The tablets were produced at a compression of 3500 pounds force for 5 seconds. The tablets contained approximately 3.5 g of the mixture.

To determine the disintegration time, a tablet of the mixture was placed in a container filled with tap water at 5° C. and the time measured for the tablet to completely disintegrate. During the disintegration period considerable effervescence occurred. After 10.26 minutes, effervescence ceased, the tablet had totally disintegrated, and the resulting solution was cloudy. The results are illustrated on FIG. 2.

EXAMPLE 3

Sodium carbonate (2.1875 g) and 1.3125 g of Poly-Tergent ® 3B2 were mixed and the mixture was then compressed into tablets on the Carver press using a 0.75 inch stainless steel tabletting die. The die was lubricated periodically with sodium stearate. The tablets were produced at a force of 10,000 pounds for a period of 20 seconds. The tablets, containing approximately 3.5 g of the surfactant carbonate mixture, were then ground in a mortar and pestle to granules and the granules screened to select those having a size in the range of −16 to +60 mesh. Granules (0.8925 g) containing the mixture of sodium carbonate and Poly-Tergent ® 3B2 were then mixed with 0.7875 g $NaHCO_3$, 1.5925 g of sodium dichloroisocyanurate, 0.7875 g of adipic and 0.0525 g soluble starch. Following mixing, tablets of the mixture were produced on the Carver press at a compression of 3500 pounds force for 5 seconds. The tablets contained approximately 3.5 g of the mixture.

To determine the disintegration time, a tablet of the mixture was placed in a container filled with tap water at 5° C. and the time measured for the tablet to completely disintegrate. During the disintegration period considerable effervescence occurred. After 5.83 minutes, effervescence ceased, the tablet had totally disintegrated, and the resulting solution was cloudy. The results are illustrated on FIG. 2.

EXAMPLE 4

Sodium carbonate (0.5738 g), 2.5820 g of adipic acid, and 0.3443 g of Poly-Tergent® 3B2 were mixed and the mixture was then compressed into tablets on the Carver press using the 0.75 inch stainless steel tabletting die. The die was lubricated periodically with sodium stearate. The tablets were produced at a force of 10,000 pounds for a period of 20 seconds. The tablets, containing approximately 3.5 g of the surfactant-carbonate-acid mixture, were then ground in a mortar and pestle to granules and the granules screened to select those having a size in the range of −16 to +60 mesh. Granules containing the mixture of sodium carbonate, adipic acid, and Poly-Tergent® 3B2 (1.0675 g) were then mixed with 1.5925 g of sodium dichloroisocyanurate, 0.7875 g of sodium bicarbonate and 0.0525 g soluble starch. Following mixing, tablets of the mixture were produced on the Carver press at a compression of 3500 pounds force for 5 seconds. The tablets contained approximately 3.5 g of the mixture.

To determine the disintegration time, a tablet of the mixture was placed in a container filled with tap water at 5° C. and the time measured for the tablet to completely disintegrate. During the disintegration period considerable effervescence occurred. After 7.08 minutes, effervescence ceased, the tablet had totally disintegrated, and the resulting solution was cloudy.

EXAMPLE 5

Sodium carbonate (0.6364 g), and 2.8636 g of adipic acid, were mixed and the mixture was then compressed into tablets on the Carver press using the 0.75 inch stainless steel tabletting die. The die was lubricated periodically with sodium stearate. The tablets were produced at a force of 10,000 pounds for a period of 20 seconds. The tablets, containing approximately 3.5 g of the carbonate-acid mixture, were then ground in a mortar and pestle to granules and the granules screened to select those having a size in the range of −16 to +60 mesh. Granules (0.9625 g) containing the mixture of sodium carbonate and adipic acid were then mixed with 1.5925 g of sodium dichloroisocyanurate, 0.1050 g of Poly-Tergent® 3B2, 0.7875 g of sodium bicarbonate, and 0.0525 g soluble starch.

Following mixing, tablets of the mixture were produced on the Carver press at a compression of 3500 pounds force for 5 seconds. The tablets contained approximately 3.5 g of the mixture.

To determine the disintegration time, a tablet of the mixture was placed in a container filled with tap water at 5° C. and the time measured for the tablet to completely disintegrate. During the disintegration period considerable effervescence occurred. After 6.90 minutes, effervescence ceased, the tablet had totally disintegrated, and the resulting solution was cloudy.

What is claimed is:

1. A method for producing sanitizing compositions which comprises:
    a) admixing an alkali metal carbonate with a solid water soluble aliphatic carboxylic acid to form an acidic mixture,
    b) compressing the acidic mixture to produce a compressed form of the acidic mixture,
    c) crushing the compressed form to produce granules of the acidic mixture, and,
    d) admixing granules of the acidic mixture with an alkali metal chloroisocyanurate, and an alkali metal bicarbonate to produce a sanitizing composition.

2. The method of claim 1 accomplished by compressing the sanitizing composition to produce a compressed form.

3. The method of claim 2 in which the weight ratio of the alkali metal carbonate to the solid water-soluble aliphatic carboxylic acid in the acidic mixture is from about 0.05:1 to about 0.9:1.

4. The method of claim 3 in which the solid water-soluble aliphatic carboxylic acid is a polycarboxylic acid.

5. The method of claim 4 in which the polycarboxylic acid is selected from the group consisting of adipic acid, citric acid, oxalic acid, tartaric acid, and mixtures thereof.

6. The method of claim 1 in which the sanitizing composition has an available chlorine concentration of from about 10 to about 60 percent.

7. The method of claim 1 in which the granules of the acidic mixture have a particle size in the range of from about 2,000 to about 150 microns.

8. The method of claim 2 in which the compressed form is selected from the group consisting of tablets, rings, disks, sticks, and briquets.

9. The method of claim 8 in which the weight ratio of the alkali metal carbonate to the solid water-soluble aliphatic carboxylic acid in the acidic mixture is from about 0.1:1 to about 0.4:1.

10. The method of claim 9 in which the solid water-soluble aliphatic carboxylic acid is adipic acid.

11. A method for producing sanitizing compositions which comprises:
    a) admixing a surfactant with a solid water soluble aliphatic carboxylic acid, or an alkali metal carbonate to form a surfactant mixture,
    b) compressing the surfactant mixture to produce a compressed form of the surfactant mixture,
    c) crushing the compressed form to produce granules of the surfactant mixture, and,
    d) admixing granules of the surfactant mixture with an alkali metal dichloroisocyanurate, an alkali metal bicarbonate and to produce a sanitizing composition, with the provision that where the solid water soluble aliphatic carboxylic acid or the alkali metal carbonate is not present in the surfactant mixture, it is incorporated into the mixture at step d).

12. The method of claim 11 accomplished by compressing the sanitizing composition to produce a compressed form.

13. The method of claim 12 in which at step d) a soluble starch is incorporated into the mixture.

14. The method of claim 12 in which the surfactant is admixed with the solid water soluble aliphatic carboxylic acid at step a).

15. The method of claim 14 in which the solid water-soluble aliphatic carboxylic acid is a polycarboxylic acid is selected from the group consisting of adipic acid, citric acid, oxalic acid, tartaric acid, and mixtures thereof.

16. The method of claim 11 in which the surfactant is anionic.

17. The method of claim 11 in which the surfactant is nonionic.

18. The method of claim 12 in which the surfactant is admixed with the alkali metal carbonate at step a).

19. The method of claim 12 in which the compressed form is selected from the group consisting of tablets, rings, disks, sticks and briquets.

* * * * *